United States Patent [19]

Gambale

[11] Patent Number: 4,763,647
[45] Date of Patent: Aug. 16, 1988

[54] DUAL COIL STEERABLE GUIDEWIRE

[75] Inventor: Richard A. Gambale, Tyngsboro, Mass.

[73] Assignee: C. R. Bard, Inc., Murray Hill, N.J.

[21] Appl. No.: 847

[22] Filed: Jan. 6, 1987

[51] Int. Cl.[4] ............................................. A61B 6/00
[52] U.S. Cl. .................................. 128/657; 128/772; 604/164
[58] Field of Search .................. 128/657, 772; 604/95, 604/164, 170, 280, 282

[56] References Cited

U.S. PATENT DOCUMENTS

| | | | |
|---|---|---|---|
| 3,749,086 | 7/1973 | Kline et al. ............................ | 604/95 |
| 4,080,706 | 3/1978 | Heilman et al. ...................... | 128/772 |
| 4,244,362 | 1/1981 | Anderson ............................. | 128/772 |
| 4,545,390 | 10/1985 | Leary ................................... | 128/772 |
| 4,619,274 | 10/1986 | Morrison ............................. | 128/772 |

Primary Examiner—Edward M. Coven
Assistant Examiner—Randy Citrin
Attorney, Agent, or Firm—Wolf, Greenfield & Sacks

[57] ABSTRACT

A steerable guidewire has an elongate main wire having a tapered distal portion and a helical coil mounted about the distal portion. The distal end of the coil extends beyond the distal tip of the tapered distal portion of the main wire. An inner helical coil is disposed within the outer coil is secured at its proximal end to the distal tip of the tapered distal portion of the main wire and at its distal end to the distal end of the outer coil. The device does not have a separate safety wire, the inner coil serving as the sole safety connection between the main wire and the outer coil. The omission of the conventional safety wire and the use of the dual coil construction provides a tip which is equally flexible in all directions. Gradual selected transitions in stiffness may be achieved by varying the spacing of the individual turns of the inner and outer coils. The guidewire also provides for a change in the radiopacity of the distal portion of the guidewire to provide a more radiopaque segment at the distal portion than at the more proximal portions by forming the inner coil from a more radiopaque material than the outer coil.

10 Claims, 1 Drawing Sheet

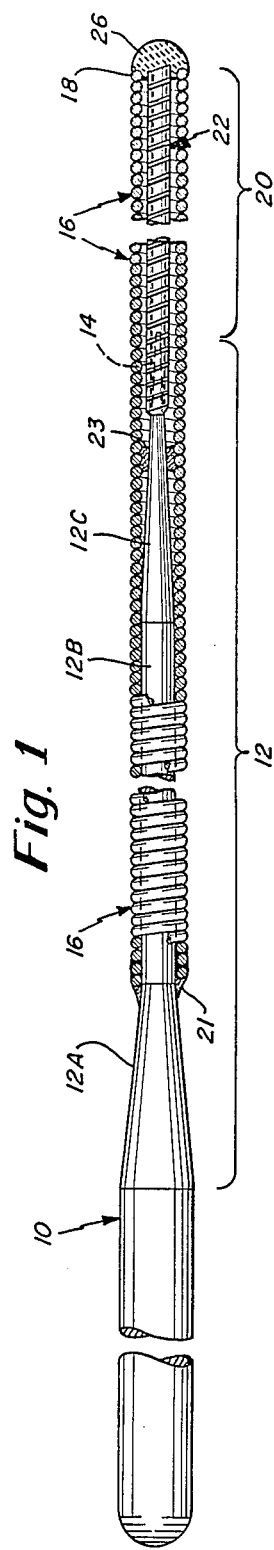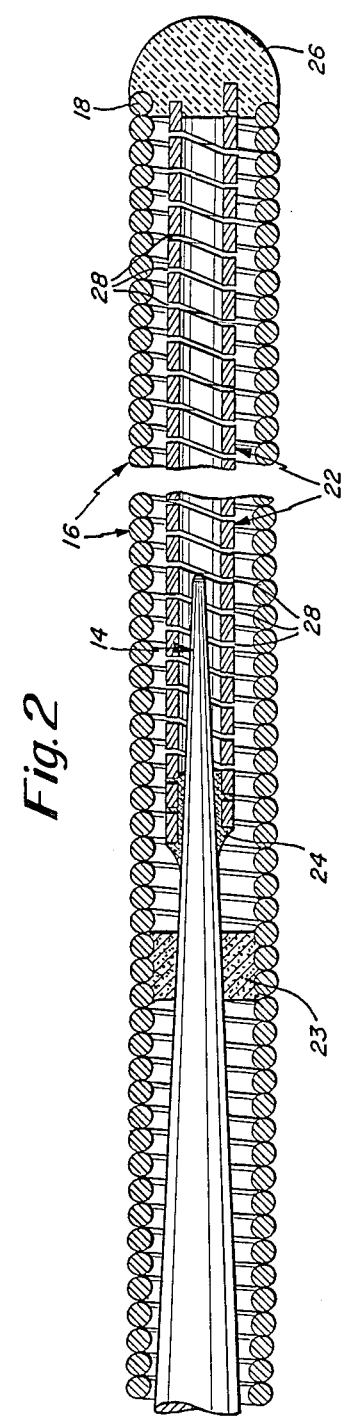
Fig. 1
Fig. 2

DUAL COIL STEERABLE GUIDEWIRE

FIELD OF THE INVENTION

This invention relates to guidewires used in surgical procedures, for example, to guide and place a catheter in a blood vessel.

BACKGROUND OF THE INVENTION

This invention relates to guidewires such as are commonly used in the placement of catheters at various locations in a patient's cardiovascular system. Typically, the guidewire is placed percutaneously into the blood vessel and a catheter having a lumen adapted to receive the guidewire is advanced over the guidewire. For example, the guidewire may be of the small diameter steerable type disclosed in U.S. Pat. No. 4,545,390 to Leary. The guidewire disclosed in the Leary patent is useful particularly in guiding small diameter catheters into distally located, small blood vessels such as the coronary arteries. The guidewire has a main wire with a tapered distal portion and a helical coil mounted to and about the tapered distal portion. The coil may extend distally beyond the distal tip of the tapered portion of the main wire and a safety wire may be provided to connect the distal tip of the main wire with the distal tip of the coil. The safety wire assures that if the distal portion of the spring breaks, it will remain attached to the guidewire so that the broken distal portion can be withdrawn from the patient.

In some instances, the safety wire presents some disadvantage in that it imparts additional stiffness to the distal tip of the guidewire. Additionally, the use of a separate safety wire tends to give the distal tip of the wire a directional characteristic, so that it will tend to bend more readily along a particular plane than in other directions. In some cases, the directional characteristic resulting from the use of the safety wire is undesirable in that it can be difficult to control the positioning of the tip. Therefore, it is desirable to provide a guidewire construction with a tip having less stiffness and in which the tip is equally flexible in all directions, while maintaining a safety connection between the main wire and the coil.

Another desirable feature is to provide a guidewire in which the distal end has a graduated stiffness transition so as to avoid kinking and possible trauma to the blood vessel.

Guidewires typically are advanced and placed in a patient's vascular system while monitoring the position of the guidewire fluoroscopically. It is desirable that the guidewire be sufficiently opaque to x-rays to provide a clear indication of the location and position of the guidewire but without obstructing the fluoroscopic image of the more proximally located portions of the blood vessel in which the guidewire is placed. Thus, there may be instances in which a greater radiopacity is preferred for the distal portion of the coil.

Another disadvantage which results from the use of a safety ribbon in the guidewire is that it results in relatively little strain relief in the event that the safety ribbon breaks, as may occur under a tensile load or when forming a curve in the distal end of the coil.

It is among the general objects of the invention to provide an improved guidewire construction which avoids the foregoing difficulties while providing the foregoing advantages.

SUMMARY OF THE INVENTION

The guidewire includes an elongate main wire having a tapered distal region. An outer helically wound coil is mounted on the distal region of the main wire about the tapered region, with the distal end of the coil extending distally beyond the distal tip of the main wire. A second coil having a smaller outer diameter than the inner diameter of the outer coil is enclosed within the outer coil and is connected at its proximal end to the distal end of the tapered region of the main wire. The distal tip of the inner coil is connected to the distal tip of the outer coil at a generally hemispherical bead which defines the distal tip of the guidewire. The inner coil serves as the sole safety means for the guidewire, there being no other safety wire connecting the distal tip of the outer coil with the distal end of the main wire. The flexibility of the composite inner and outer coils is uniform in all directions. The degree of flexibility may be varied as desired by spacing selected of the adjacent coils in one or both of the inner and outer coils to provide the desired composite flexibility characteristics. The inner coil may be formed from an alloy which is more radiopaque than that from which the outer coil is formed so as to provide a distal segment having greater radiopacity than the more proximal portions of the guidewire.

It is among the general objects of the invention to provide an improved guidewire construction by which a guidewire may have a distal portion having a high degree of omnidirectional flexibility.

Another object of the invention is to provide an improved guidewire construction in which the distal portion of the guidewire is provided with a smoothly graduated transition and flexibility.

A further object of the invention is to provide an improved guidewire construction by which the distal tip of the guidewire is more highly radiopaque than the more proximal portions of the distal tip region of the guidewire.

Another object of the invention is to provide an improved guidewire construction in which the distal coil region provides an increased strain relief to axial and bending loads.

Another object of the invention is to provide an improved guidewire construction in which the foregoing objects are achieved without the use of a conventional safety wire.

DESCRIPTION OF THE DRAWING

The foregoing and other objects and advantages of the invention will be appreciated more fully from the accompanying drawings in which:

FIG. 1 is a fragmented, sectional illustration of the guidewire; and

FIG. 2 is an enlarged fragmented sectional illustration of the distal portion of the guidewire.

DESCRIPTION OF THE PREFERRED EMBODIMENT

As shown in the drawing, the guidewire includes a main wire 10 which may be formed from stainless steel. The main wire 10 extends over most of the overall length of the guidewire, which may be between about 145 to 300 cm long. The distal region 12 of the main wire 10 is tapered and terminates in a tip 14. By way of example, the distal region 12 may be of the order of 25 to 30 cm long. The taper may be formed in steps, for example, to include a proximal first tapered segment 12A, a second portion 12B which may be of uniform diameter and a third portion 12C which is tapered. By way of example, the main wire 10 may be of the order of 0.016" diameter and the section 12B may be of the order of 0.008" diameter. The tip 14 preferably terminates in a diameter of the order of 0.001". The tapered distal region 12 may be formed by centerless grinding.

An outer coil 16 is helically wound and is mounted to the main wire 10 about the distal region 12. The outer coil 16 is sufficient long so that the distal tip 18 of the coil 16 extends beyond the distal tip 14 of the main wire 10, thereby defining a distal segment 20. The proximal end of the coil 16 is secured to the main wire 10 adjacent the region where the wire begins to taper, such as by brazing as indicated at 21. The outer coil 16 also is secured to the main wire 10 at a more distal location, such as by brazing it to the distal tapered portion 12C, as indicated at 23.

The guidewire includes an inner coil 22 which extends along the distal segment 20 and is connected at its proximal and distal ends to the region of the tip 14, of the main wire as by brazing at 24, and the distal tip 18 of the outer coil, respectively. The distal tip of the guidewire may be formed to include a welded bead 26 which is smoothly rounded and welds the coils 16, 22 together. In accordance with the invention, the inner coil 22 comprises the sole connection between the distal tip 14 of the main wire and the distal tip 18 of the outer coil 16. In one embodiment of the invention, the outer and inner coils 16, 22 are wound in opposite directions. That may be desirable in a small diameter (less than about 0.020") guidewire of the type described in the Leary patent. The torsional rigidity of the composite distal tip is enhanced in both rotational directions, that is, the device tends to transmit rotation about equally in both directions. In another embodiment (illustrated in the drawing) the outer and inner coils 16, 22 are wound in the same direction. That configuration provides advantages in the axial strength of the guidewire and in the failure mode under the influence of an axial load to provide an additional measure of safety. Should the distal weld at the hemispherical tip 24 break, the continued axial load on the outer coil 16 will continue to stretch the outer coil 16 which causes the diameter of the outer coil to constrict about the inner coil 22. When the outer and inner coils 16, 22 are wound in the same direction, the outer coil 16 tends to interlock with the inner coil 22 so that the coils 16, 22 can cooperate in resisting further axial stretching.

The spacing on the outer and inner coils 16, 22 may be varied to provide a wide range of flexibility of the guidewire. In the illustrative embodiment, the spacing 28 of the individual turns in inner coil 22 is of the order of 0.0002". The spacing on one of the coils may be different from the spacing on the other and the spacing on one or both of the coils may be such that portions of the coil have different spacing than other portions of the coil, thereby to vary the flexibility characteristics of the device.

The inner coil 22 does not impart any bias to the direction in which the distal segment 20 flexes because it is free of conventional safety wires.

The drawing illustrates further the manner in which the outer and inner coils 16, 22 may be arranged to provide for a smooth transition and progressively increasing flexibility in a distal direction.

In another aspect of the invention, the inner and outer coils 22, 16 may be formed from a radiopaque alloy. For example, the inner and outer coils may be formed from an alloy of 80% platinum, 15% rhodium and 5% ruthenium. That alloy has been found to provide a suitably malleable property which enables a curve to be formed relatively easily in the distal tip of the coil. Alternately, an alloy of 92% platinum and 8% tungsten may be used. In that configuration, the entire length of the outer coil will be radiopaque with the distal segment having a higher radiopacity. In alternative embodiments, the portion of the outer coil 16 proximal of the distal segment 20 may be made less opaque to x-rays by forming the outer coil 16 from stainless steel and the inner coil 22 from the radiopaque alloy. That configuration provides a highly radiopaque segment at the distal segment 20 and a less radiopaque portion proximal of the distal segment. With that arrangement, the distal segment 20 will be highly radiopaque and will be clearly visible under fluoroscopy. The more proximal segment of the outer coil 16 will have less radiopacity and will present less of a visual obstruction to those portions of the blood vessel located proximally of the distal segment 20.

By way of further illustrative example, the guidewire may be of the order of 185 cm long. The main wire may be of the order of 0.014"–0.018" diameter. In a preferred embodiment, the main wire is 0.016" diameter and the outer coil is 0.012" diameter. The stepped down configuration from the larger diameter main wire to the smaller outer diameter for the outer coil provides a guidewire having a high degree of torsional rigidity by which angular rotation of the proximal end of the guidewire may be transmitted substantially fully to the distal end, but in which the distal end is of a smaller diameter so that it may obstruct less of the catheter lumen through which it passes, particularly in the region of a dilatation balloon, thereby providing for a larger annular flow area in the catheter lumen and enabling better distal pressure measurement and dye injection. In the illustrative embodiment, the outer coil 16 may be formed from 0.002" diameter wire wound to a coil diameter of 0.012". The inner coil may have an outer diameter of 0.006" and is formed from rectangular cross-section ribbon 0.0015"×0.003" diameter. The ribbon configuration is preferred in the forming of the inner coil because the ribbon is more resistant to stretching out than round cross-sectional wire and also enables the inner coil to be formed with a smaller outer diameter.

From the foregoing it will be appreciated that I have described an improved construction for a guidewire in which the distal tip has omnidirectional flexibility while maintaining a safety connection to the distal tip of the outer coil, but without using the conventional safety wire. Additionally, the guidewire construction provides an arrangement for a smooth and gradual increase in flexibility toward the distal tip as well as an arrangement in which the radiopacity at the tip is sufficient to provide good fluoroscopic monitoring but which does not obstruct the fluoroscopic view of portions of the blood vessel immediately adjacent the distal tip of the guidewire. It should be understood, however, that the foregoing description of the invention is intended merely to be illustrative thereof and that other modifications and embodiments may be apparent to those skilled in the art without departing from its spirit.

Having thus described the invention, what I desire to claim and secure by letters patent is:

1. A guidewire comprising:

a main wire having a proximal end and a distal end and a distal tapered region;

a first outer helical coil mounted about the tapered region of the main wire and being connected to the main wire at the proximal end of the coil, the distal end of the coil extending distally beyond the distal end of the main wire;

a second, inner, helical coil having a smaller diameter than the first coil and being disposed within the first coil, the second coil being connected at its proximal end to the distal region of the main wire and at its distal end to the distal end of the outer coil;

the second, inner, coil defining a safety means to maintain connection between the main wire and a distal portion of the first coil in the event of breakage of the first coil, said second coil comprising the sole safety means connecting the distal end of the outer coil with the main wire;

the outer and second coils being wound in the same direction.

2. A guidewire as defined in claim 1 wherein said outer coil is connected to the main wire at a location adjacent the distal end of the main wire.

3. A guidewire as defined in claim 2 wherein the outer coil is longer than the second coil.

4. A guidewire as defined in claim 3 wherein one of the coils is formed from a more radiopaque material than the other of the coils.

5. A guidewire as defined in claim 4 wherein the inner coil is more radiopaque than the outer coil.

6. A guidewire as defined in claim 5 wherein the inner coil is formed from an alloy comprising 80% platinum, 15% rhodium and 5% ruthenium.

7. A guidewire as defined in claim 5 wherein the inner coil is formed from an alloy comprising 92% platinum and 8% tungsten.

8. A guidewire as defined in claims 1 or 2 wherein at least one of the coils is formed from an alloy comprising 80% platinum, 15% rhodium and 5% ruthenium.

9. A guidewire as defined in claims 1 or 2 wherein at least one of the coils is formed from an alloy comprising 92% platinum and 8% tungsten.

10. A guidewire as defined in claims 1 or 2 wherein the second coil is formed from wire having a flat rectangular cross section.

* * * * *